United States Patent
Durand

(10) Patent No.: US 11,826,571 B2
(45) Date of Patent: Nov. 28, 2023

(54) SYSTEMS AND METHODS FOR CLOSED LOOP CONTROL TO ENSURE A CONSTANT CURRENT OUTPUT WITH A CHANGING LOAD RESISTANCE

(71) Applicant: CASE WESTERN RESERVE UNIVERSITY, Cleveland, OH (US)

(72) Inventor: Dominique M. Durand, Solon, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 225 days.

(21) Appl. No.: 17/462,718

(22) Filed: Aug. 31, 2021

(65) Prior Publication Data

US 2021/0393962 A1 Dec. 23, 2021

Related U.S. Application Data

(60) Division of application No. 16/559,968, filed on Sep. 4, 2019, now Pat. No. 11,191,965, which is a continuation of application No. 15/353,923, filed on Nov. 17, 2016, now Pat. No. 10,441,790.

(60) Provisional application No. 62/329,343, filed on Apr. 29, 2016, provisional application No. 62/256,758, filed on Nov. 18, 2015.

(51) Int. Cl.
*A61N 1/36* (2006.01)
*A61N 1/05* (2006.01)
*G05B 19/042* (2006.01)
*A61N 2/00* (2006.01)
*A61N 2/02* (2006.01)
*G16H 20/40* (2018.01)
*G16H 20/30* (2018.01)

(52) U.S. Cl.
CPC ....... *A61N 1/36128* (2013.01); *A61N 1/3614* (2017.08); *A61N 1/3615* (2013.01); *A61N 1/36139* (2013.01); *A61N 2/006* (2013.01); *A61N 2/02* (2013.01); *G05B 19/042* (2013.01); *G16H 20/30* (2018.01); *G16H 20/40* (2018.01); *A61N 1/0551* (2013.01); *G05B 2219/45117* (2013.01)

(58) Field of Classification Search
CPC ............ A61N 1/36128; A61N 1/36139; A61N 1/0551; G05B 19/042
See application file for complete search history.

*Primary Examiner* — Paula J Stice
(74) *Attorney, Agent, or Firm* — TAROLLI, SUNDHEIM, COVELL & TUMMINO, LLP

(57) ABSTRACT

A closed loop control system automatically ensures that an output of a device is constant. The system can receive an input to set a fixed value for a variable (e.g., a current, a heart rate, a tissue perfusion, an ion level, etc.), and this variable can be delivered to a feedback component. The system can also include the device to deliver the variable to a load. The feedback component can be coupled to the delivery device to sample the output of the delivery device at different times. Based on the sampling, the feedback component can vary a property of the delivery device related to the delivery of the variable to the load to ensure that the variable remains constant at the fixed value. In some instances, the system can be implemented as a stimulator that delivers the constant current of a current source and has a low output impedance of a voltage source.

9 Claims, 5 Drawing Sheets

SYSTEMS AND METHODS FOR CLOSED LOOP CONTROL TO ENSURE A CONSTANT CURRENT OUTPUT WITH A CHANGING LOAD RESISTANCE

RELATED APPLICATIONS

This application is a divisional of U.S. Ser. No. 16/559,968 (now U.S. Pat. No. 11,191,965), entitled "SYSTEMS AND METHODS FOR CLOSED LOOP CONTROL TO ENSURE A CONSTANT CURRENT OUTPUT WITH A CHANGING LOAD RESISTANCE", filed Sep. 4, 2019, which is a continuation of U.S. Ser. No. 15/353,923 (now U.S. Pat. No. 10,441,790), entitled "SYSTEMS AND METHODS FOR CLOSED LOOP CONTROL TO ENSURE A CONSTANT CURRENT OUTPUT WITH A CHANGING LOAD RESISTANCE", filed Nov. 17, 2016, which claims the benefit of U.S. Provisional Application No. 62/329,343, entitled "SYSTEMS AND METHODS FOR CLOSED LOOP CONTROL," filed Apr. 29, 2016, and also claims the benefit of U.S. Provisional Application No. 62/256,758, entitled "CONSTANT CURRENT POWER VOLTAGE SOURCE STIMULATOR", filed Nov. 18, 2015, which are all hereby incorporated by reference in their entirety for all purposes.

TECHNICAL FIELD

The present disclosure relates generally to closed loop control, and, more specifically, to systems and methods for automatic closed loop control to ensure that an output of a device (e.g., a current) is constant when a resistance of a load changes.

BACKGROUND

Electrical stimulation is generally the application of an electrical current to a load using a current source or a voltage source. A voltage source has a low output impedance and provides a constant voltage and variable current, while a current source has a high output impedance and provides a constant current and variable voltage. In applications where the load is neural tissue, traditionally, a constant current source has been used to deliver a known constant current in the presence of a constantly changing tissue resistance. However, application of the constant current can lead to an accumulation of charge at the tissue-electrode interface, which can cause irreversible electrochemical reactions that can damage the tissue or the electrode.

SUMMARY

The present disclosure relates generally to closed loop control, and, more specifically, to systems and methods for automatic closed loop control to ensure that an output of a device is constant. In some instances, the automatic closed loop control can be used with a stimulator to control a current being applied to a load (e.g., biological tissue). An operator (e.g., a clinician) can preset the current, and the closed loop control can automatically control the power into the load to ensure that the preset current is delivered to the load. Accordingly, the stimulator can provide a constant current, while offering a low output impedance. In other instances, the automatic closed loop control can be used to ensure that any variable that is set at a fixed level by an input, including heart rate, tissue perfusion, ion level, and the like, remains at the fixed level. As an example, a device can automatically control heart rate by stimulating the vagus nerve with the heart rate being the feedback variable.

In one aspect, the present disclosure can include a system that ensures that an output of a device is constant. The system can include a device to deliver a variable to a load. The system can also include a feedback component, coupled to the delivery device, to sample the output of the delivery device at different times. Based on the sampling, the feedback component can vary a property of the delivery device related to the delivery of the variable to the load to ensure that the variable remains constant at the fixed value. The feedback component can receive an input to set the fixed value for the variable (e.g., a current, a heart rate, a tissue perfusion, an ion level, etc.).

In another aspect, the present disclosure can include a method for ensuring that an output of a device is constant. The method includes: setting a constant output to provide to a load, wherein the output is provided with a low output impedance; sampling the variable associated with the output; and controlling a property related to the output based on the sampled variable so that the output to the load remains constant. In some instances, the method can be used in connection with a stimulator device that provides a constant current with a low output impedance, achieving properties of both a current source and a voltage source. For example, the load can include one or more nerves and the output can ensure that a constant current is applied to stimulate the one or more nerves with a low output impedance to eliminate the formation of harmful electrochemical reaction products.

In a further aspect, the present disclosure can include a stimulator with a constant output current and a low output impedance. The stimulator can include a voltage source to provide a set point voltage. The stimulator can also include an adjustable gain amplifier to receive the set point voltage and provide the output current independent of a impedance of a load. The stimulator can also include a feedback component, coupled to the adjustable gain amplifier, to sample a power at different times and vary a gain of the adjustable gain amplifier based on the sampled power.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
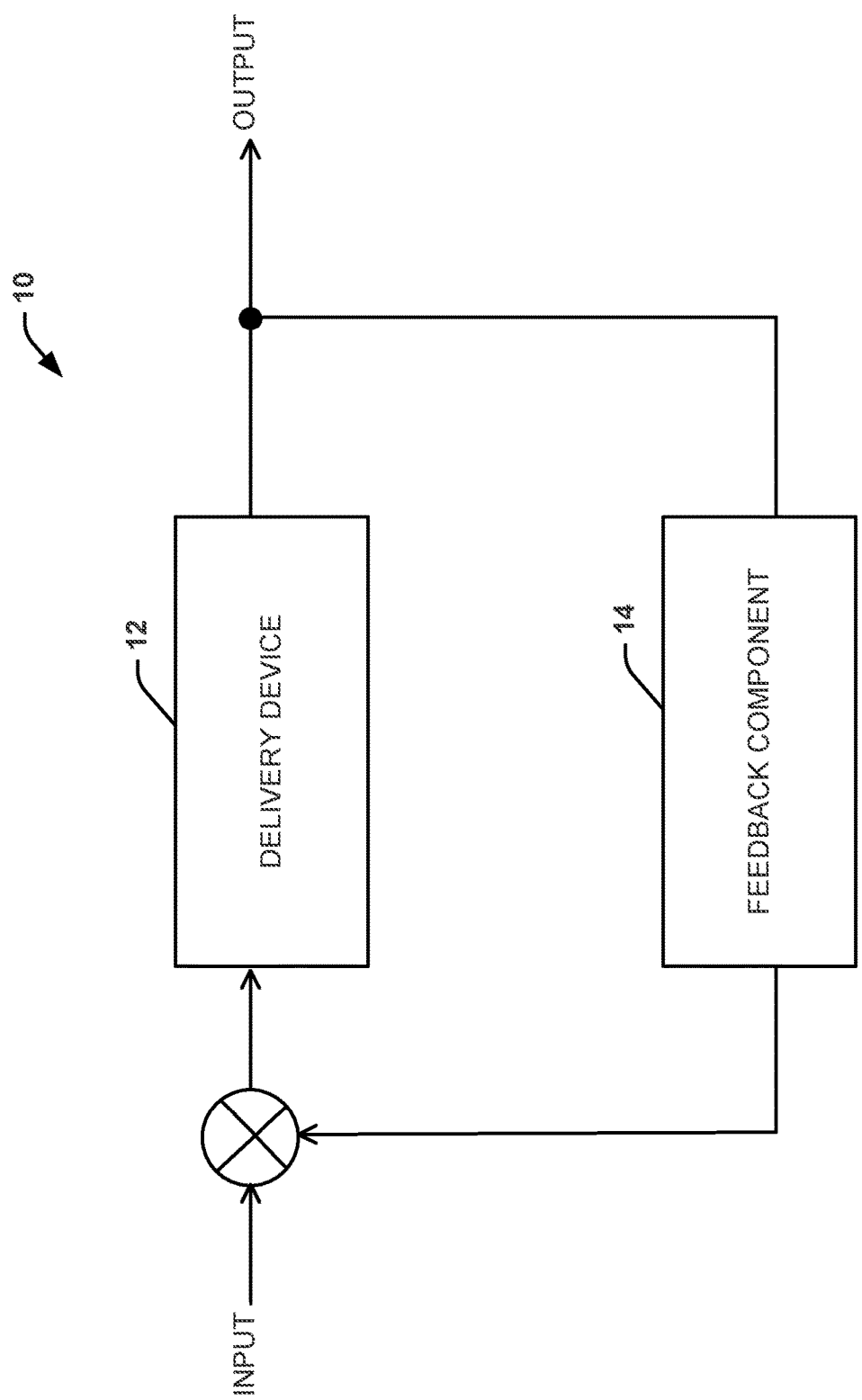
FIG. 1 is a block diagram showing an example of a closed loop control system according to an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "closed loop control" refers to automatic changes to a variable that are made to a variable based on a detected output to ensure that an input remains constant.

As used herein, the term "automatic" refers to a device or process operating by itself with little or no direct human control.

As used herein, the term "variable" refers to an element that varies or changes. Examples of variables include, but are not limited to, current, current power, heart rate, tissue perfusion rate, and ion or other biometric level.

As used herein, the term "stimulator" refers to an analog or digital device that delivers electrical current to a load. The stimulator can have characteristics of a current source (constant current application) and a voltage source (low output impedance).

As used herein, the term "load" refers to an element that is connected to the output of the stimulator. In some instances, the load can include an interface between an electrode and biological tissue (the "electrode-tissue interface"). For example, the biological tissue can include one or more nerves.

As used herein, the term "nerve" can refer to one or more fibers that employ electrical and chemical signals to transmit motor, sensory, and/or autonomic information from one body part to another. A nerve can refer to either a component of the central nervous system or the peripheral nervous system.

As used herein, the term "impedance" refers to the measure of the opposition that a circuit presents to a current when a voltage is applied. The term "resistance" may be used interchangeably with impedance herein.

As used herein, the term "output impedance" refers to the opposition exhibited by output terminals of the stimulator device and can be the impedance looking back into the output terminals.

As used herein, the term "load resistance" refers to the "input impedance" or the opposition to current flow from the stimulator device, which can be variable over time. As an example, the load resistance can be provided by the biological tissue ("tissue resistance").

As used herein, the term "sampling" refers to the reduction of a continuous stimulation signal to a discrete value at a point in time.

As used herein, the term "coupled" can refer to two circuit elements being electrically connected to each other so that current flows therebetween in at least one direction.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

Traditionally, neural stimulation has been conducted with a current source to deliver a known current to a continually changing tissue resistance. Generally, a regulated current source includes a voltage source, a current monitoring circuit, and a feedback circuit. As the tissue resistance changes, the feedback circuit instantaneously adjusts the voltage to maintain a constant current, thereby generating a high output impedance. However, if the adjustment is delayed in time, the output impedance can remain low, while maintaining the constant current delivered. Advantageously, the present disclosure describes a stimulator with characteristics of a current source (constant current application) and a voltage source (low output impedance).

The systems and methods described herein provide automatic closed loop control to ensure that an output of a device (e.g., the current provided by a stimulator) is constant. The stimulator also provides a low output impedance to reduce the potential for damage at the electrode-tissue interface due to irreversible electrochemical reaction products. As opposed to the regulated current source, the feedback circuit of the stimulator described herein does not take instantaneous current measurements. Instead, the current measurements are taken over a period of time to estimate the power of the current delivered, which accounts for a change in resistance of the load. The stimulator has application where the load resistance changes slowly and the circuit does not require instantaneous adjustment. The stimulator can operate as an analog or digital electrical circuit or even find application as a magnetic stimulator. Moreover, the automatic closed loop control of the systems and methods described herein can be used to control outputs and variables other than current, such as heart rate, tissue perfusion rate, ion or other biometric level, or the like.

III. Systems

One aspect of the present disclosure can include a closed loop control system 10 (FIG. 1) that can ensure that an output of a delivery device 12 is constant. The system 10 can include an input that can set a fixed value for a variable (e.g., a current, a heart rate, a tissue perfusion, an ion level, etc.). As an example, the input can be set by a user (e.g., a clinician) to a certain value. In another example, the input can be set by the system 10 based on one or more characteristics of a load. The system 10 can also include a delivery device 12 to deliver a signal based on the variable as an output. In some examples, the output can be delivered to the load. The system 10 can also include a feedback component 14, coupled to the delivery device 12, to sample the output of the delivery device 12 at different times. In some instances, the sampling is not done instantaneously and, instead, is done over a window of time. Based on the sampling, the feedback component 14 can vary a property of the delivery device 12 related to the delivery of the signal to the load to ensure that the variable remains constant at the fixed value. In some instances, the system 10 can ensure that the output does not vary when a resistance of the load changes.

In some instances, system 10 can be used with a stimulator to control a current being applied to a load (e.g., biological tissue). An operator (or clinician) can preset the current and the system 10 can automatically control the power into the load to ensure that the preset current is delivered to the load. Accordingly, the stimulator can provide a constant current, while offering a low output impedance. In other instances, the system 10 can be used to ensure that any variable that is set at a fixed level by an input, including heart rate, tissue perfusion rate, ion or other biometric level, and the like, remains at the fixed level. As an example, the delivery device 12 can automatically control heart rate by stimulating the vagus nerve, and the variable fed into the feedback component 14 can be a resulting heart rate.

Figure 2:
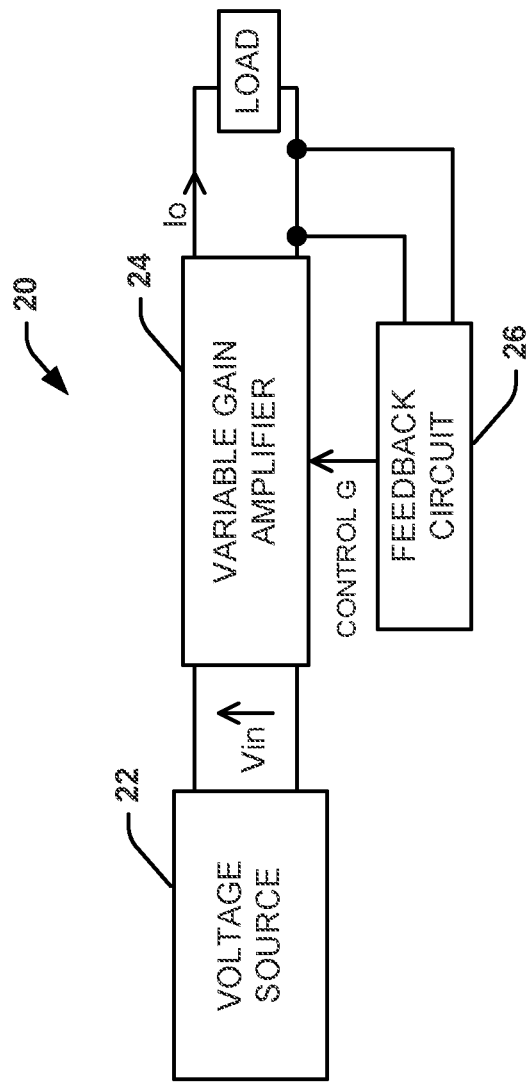
FIG. 2 is a block diagram showing a stimulator system that can employ the closed loop control system in FIG. 1 to provide a constant current of a current source and a low output impedance of a voltage source.

As shown in FIG. 2, the closed loop control can be used with a stimulator 20 that can provide an analog current (Io) to a load. The stimulator 20 can provide a constant current of a current source and a low output impedance of a voltage source. The stimulator 20 can include a voltage source 22, a variable gain amplifier 24, and a feedback circuit 26. The feedback circuit 26 can measure the current through the load over a window of time to estimate the power of the current over the window of time. The feedback circuit 26 does not measure an instantaneous amplitude of the current, like a traditional current source with infinite output impedance. Instead, the power estimate over the time window enables the output impedance of the stimulator 20 to remain low, but ensures the delivery of the constant current.

Advantageously, the stimulator 20 can be used in neural stimulation applications, especially using high frequency alternating current (HFAC) waveforms. The stimulator 20 can deliver a known, constant current to the tissue in the presence of a changing tissue resistance. The stimulator 20 can also reduce the accumulation of charge at the tissue-electrode interface, which is common in traditional neural stimulation applications. For example, the reduction of charge accumulated at the tissue-electrode interface can reduce the occurrence of irreversible electrochemical reactions that can damage the electrode or the tissue.

As shown in FIG. 2, the voltage source 22 feeds a set point voltage input (Vo) into a variable gain amplifier 24. The variable gain amplifier 24 is connected to the load to supply a known input current (Io) to the load. For example, the input current (Io) can be selected by a user (e.g., a clinician) for a certain neural stimulation application. The load can be associated with a load resistance (Ro) that may change. The feedback circuit 16 can determine a change in the load resistance (Ro) and control the gain (G) of the variable gain amplifier 24 accordingly to ensure that the input current (Io) supplied to the load does not vary. In these instances, the load resistance (Ro) is assumed to change more slowly than a rate of integration of the feedback circuit 26.

Figure 3:
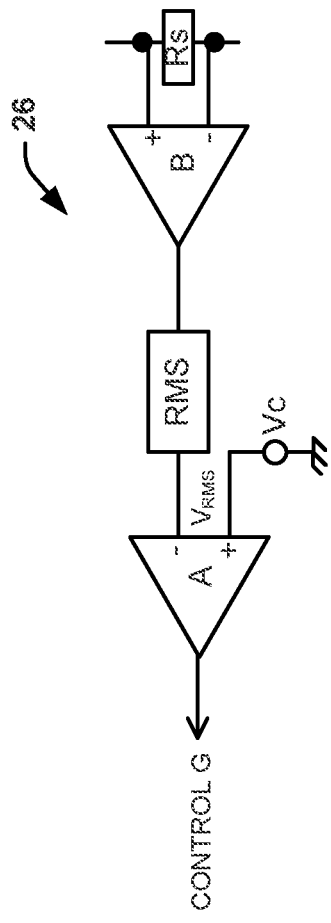
FIG. 3 is a block diagram of an example of a feedback circuit that can be used in the stimulator system in FIG. 2.

An example of the feedback circuit 26 is shown in FIG. 3. The feedback circuit 26 can include a resistor in series with the load, or series resistance (Rs), to sample the current through the load. The current through Rs is then amplified with a differential amplifier with a gain B. The output of the amplifier B is rectified and integrated to obtain a voltage $V_{RMS}$ related to the power (RMS) of the current into the load. For example:

$$V_{RMS} = BI_{RMS}Rs,$$

where $I_{RMS}$ is the current related to the power (RMS) of the current into the load.

The voltage $V_{RMS}$ can be compared to a preset control value (Vc). For example, the present control voltage value (Vc) can be the same as the constant set point voltage (Vo) supplied by the voltage source 22. However, the preset control value (Vc) need not be the same as the constant set point voltage (Vo). The difference between the voltage $V_{RMS}$ and the present control voltage value (Vc) is amplified by an amplifier with a very large gain A (much larger than G/KBRs) to generate a voltage $V_G$, which is used to control the gain (G) of the variable gain amplifier 24. For example:

$$G = KV_G,$$

where K is a constant.

The current related to the power (RMS) of the current into the load (or output current power) is independent of the load resistance, as:

$$I_{RMS} = Vc/BRs,$$

so that $I_{RMS}$ is constant and proportional to Vc when A is very large, such that G/KBRs is much less than A. B and Rs are fixed at constant values. Indeed, $I_{RMS}$ is also independent of the load resistance.

Figure 4:
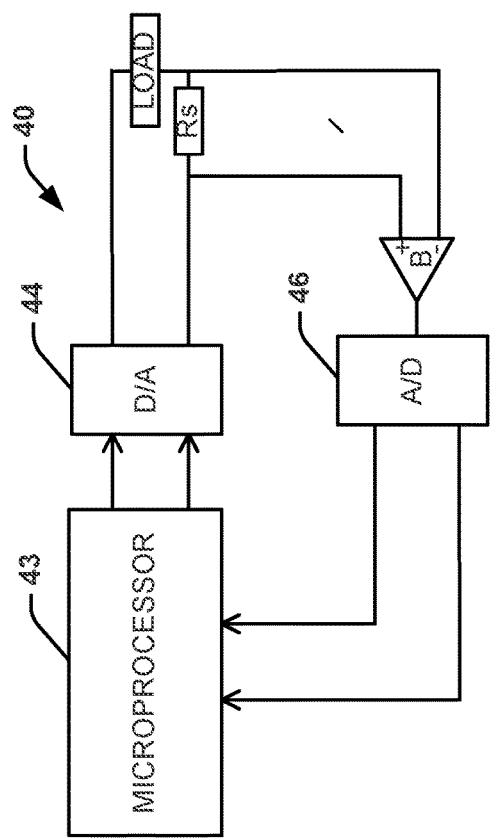
FIG. 4 is a block diagram showing a digital implementation of the stimulator system in FIG. 2.

As shown in FIG. 4, the stimulator 40 can be implemented digitally. The digital implementation of the stimulator 40 can include a microprocessor 42, a digital-to-analog converter (D/A) 44, and an analog-to-digital converter (A/D) 46. The microprocessor 42 can set a voltage (e.g., Vc) required at the input of the D/A 44. The voltage output is applied to the load. The load can have a resistance Ro. The current through the load is measured by sampling the voltage through the load. For example, as illustrated in FIG. 4, the sampling can be done by the series resistor (Rs) and one or more amplifiers with various gains. In some instances, the amplifiers can be the same as those shown in FIG. 3. The power of the signal is calculated by the microprocessor and the power is compared to the required voltage. The microprocessor 42 can change a property related to the required voltage based on the comparison.

Figure 5:
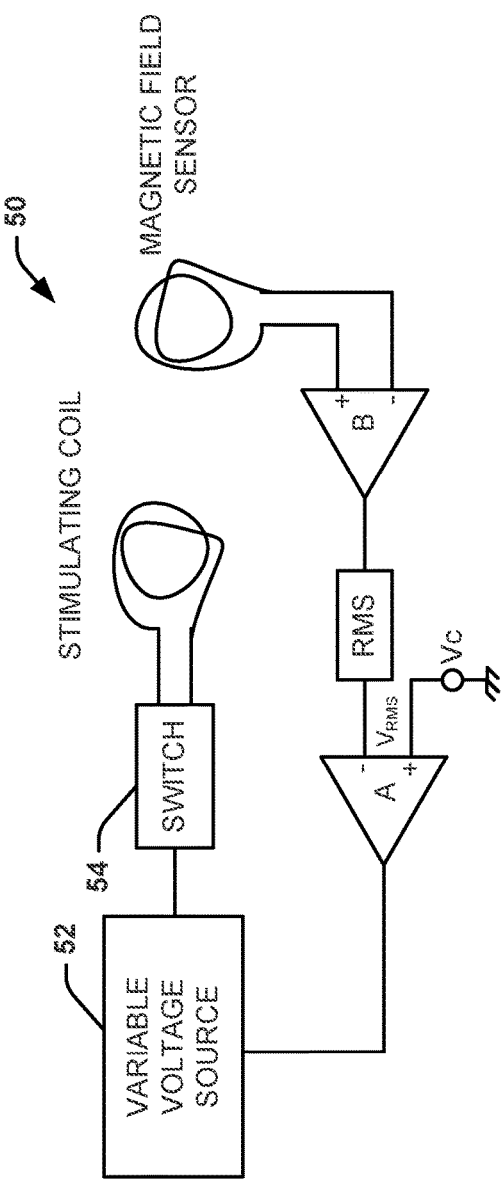
FIG. 5 is a block diagram showing the stimulator system in FIG. 2 implemented for magnetic stimulation.

The stimulator 50, as shown in FIG. 5, can be implemented for magnetic stimulation where it is difficult to maintain the generated induced power. In particular, any change in the angle of the coil (e.g., stimulator coil) or the distance to the target load can be changing. The magnetic stimulator 50 can include a variable voltage source 52 (which can be large) and a switch 54 to discharge the charge from the voltage source 52 to a coil for stimulating (stimulator coil). A monitoring coil or other sensor can detect the induced electric field at or close to the desired target and in the correct direction. For example, the monitoring coil can be a single turn coil. In other examples, other sensors can be used, such as a Hall sensor or a GMR sensor. The output of the sensor can be amplified, and the RMS value of the signal can be integrated to obtain the power of the induced electric field. The RMS value can be compared to the reference value (Vc) and the voltage source 52 can be adjusted accordingly. The magnetic stimulator 50 can be controlled by a different variable than the induced magnetic power. For example, the magnetic stimulator 50 can be applied to lower neural excitability of the brain and using the feedback can be a preset level of neural excitability.

IV. Methods

Figure 6:
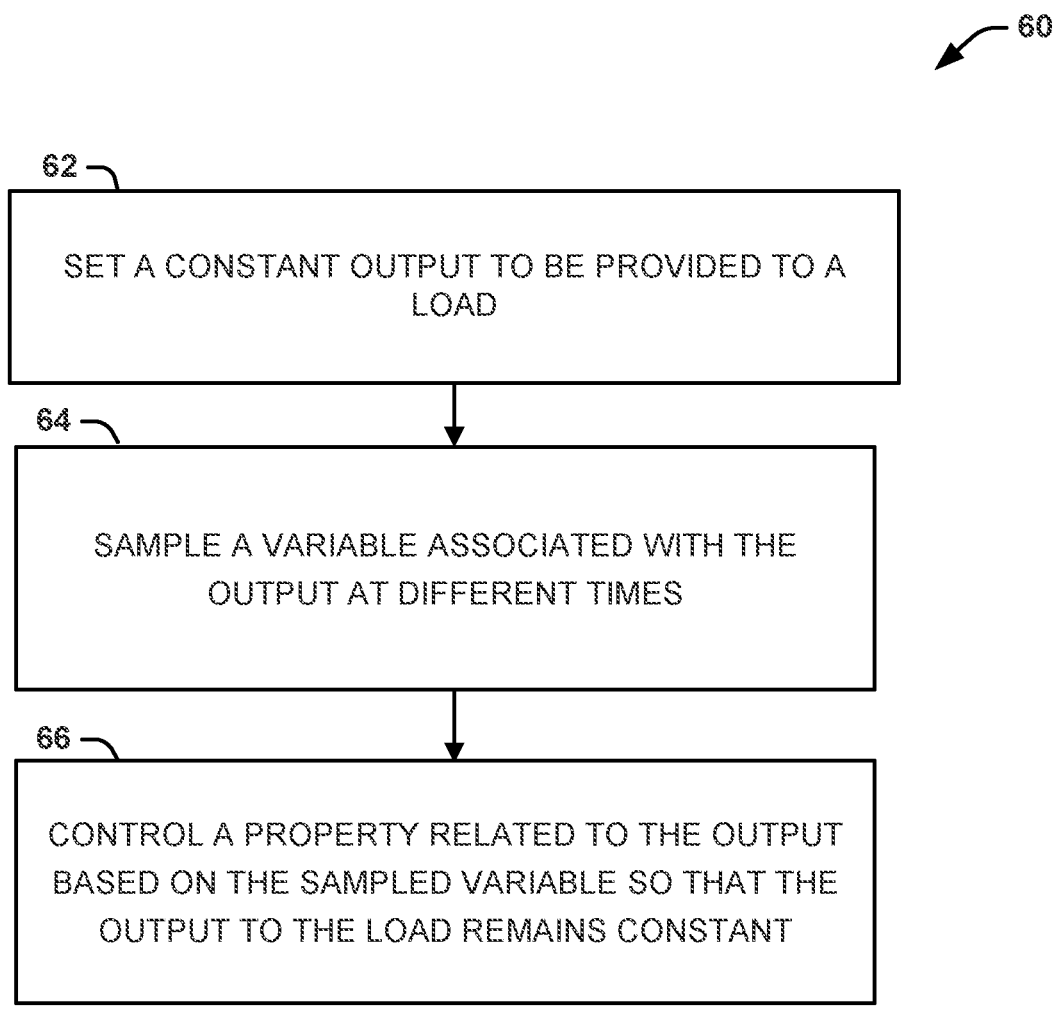
FIG. 6 is a process flow diagram of a method for ensuring that an output of a device is constant, according to another aspect of the present disclosure.

Another aspect of the present disclosure can include a method 60 (FIG. 6) for ensuring that an output of a device (e.g., a current, a heart rate, a tissue perfusion, an ion level, or the like) is constant. The method 60 can provide for closed loop control, by which a variable associated with the output is detected (e.g., by feedback component 14) and a characteristic associated with the input is adjusted (e.g., within delivery device 12) based on the detected variable associated with the output. Advantageously, the method 60 can be used to provide a stimulator device that can provide a constant current like a current source, while providing a low output impedance like a voltage source.

The method 60 can generally include the steps of: setting a constant output to provide to a load (Step 62); sampling a variable associated with the output at different times (Step 64); and controlling a property related to the output based on the sampled variable so that the output to the load remains constant (Step 66). The method 60 is illustrated as process flow diagrams with flowchart illustrations. For purposes of simplicity, the method 60 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 60.

At Step 62, a constant output is set to be provided to a load. The output can be set to a fixed value for a variable, such as current, heart rate, tissue perfusion, ion level, or the like. As an example, the input can be set be a user, such as a clinician, to a certain fixed value. In another example, the input can be set automatically based on one or more characteristics of a load. The output can be provided to the load by a device (e.g., delivery device 12 or any type of stimulator 20-50).

At Step 64, a variable associated with the output is sampled at different times (e.g., by a feedback component 14 coupled to the delivery device 12). In some instances, the sampling is not done instantaneously and, instead, is done over a window of time. At Step 66, a property related to the output can be controlled (e.g., by a portion of the delivery device 12 based on a determination by the feedback component 14) based on the sampled variable so that the output to the load remains constant at the fixed value. In some instances, when a resistance of the load changes the output does not vary.

Figure 7:
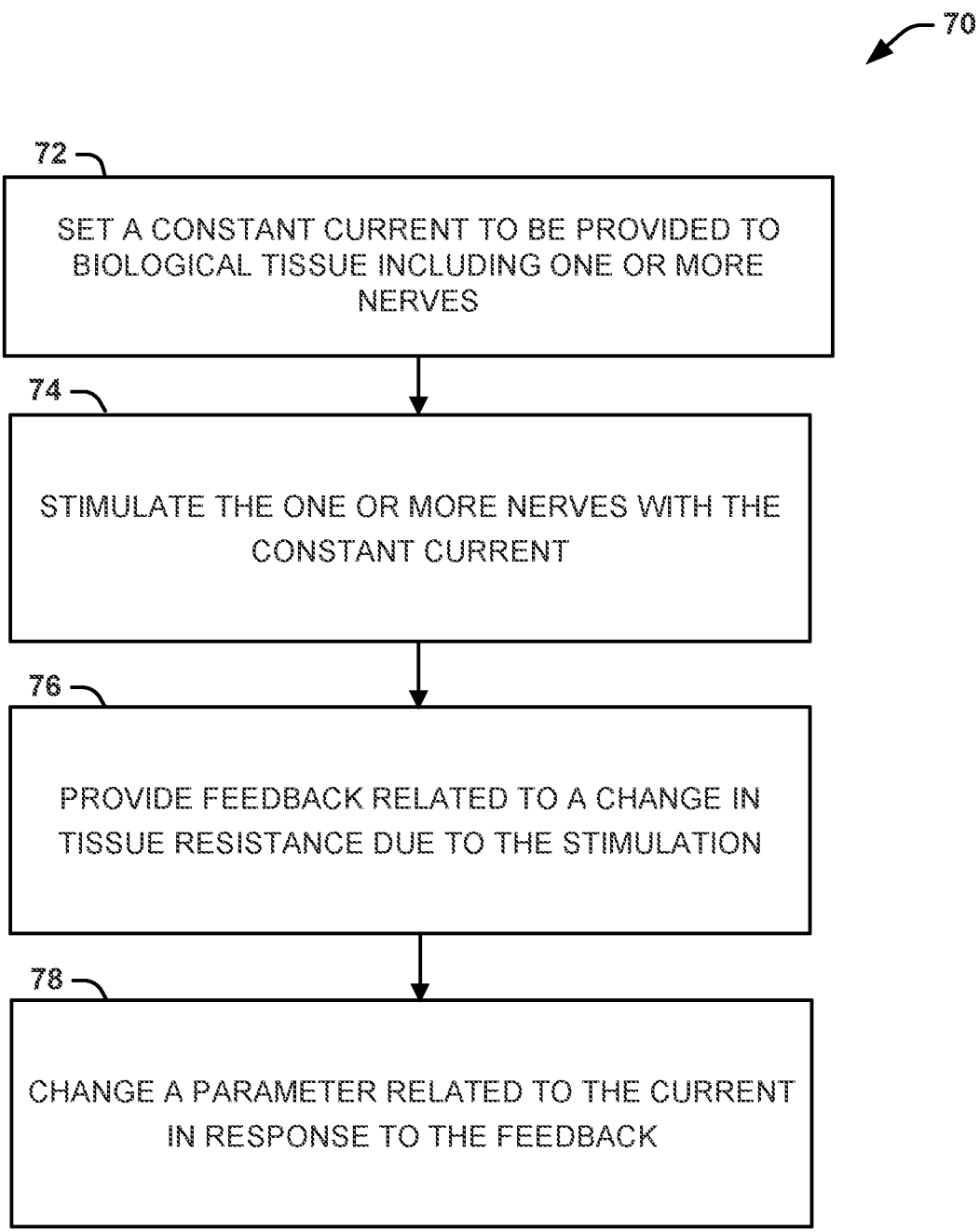
FIG. 7 is a process flow diagram showing an example method for applying a constant current for neural stimulation with a low output impedance to prevent the formation of harmful irreversible electrochemical reaction products.

An example method 70 for applying a constant current to a nerve with low output resistance is shown in FIG. 7. The method 70 can be executed, for example, by the stimulator shown in FIG. 2. At Step 72, a constant current to be provided to biological tissue including one or more nerves can be set. In some instances, the constant current can be set in response to an input from a user (e.g., a clinician). In other instances, the constant current can be set automatically. The current can be provided by the stimulator including a voltage source 22 and an associated variable gain amplifier 24, as shown in FIG. 2.

At Step 74, the one or more nerves can be stimulated with the constant current. Advantageously, with the arrangement shown in FIG. 2, the constant current can be delivered without the generation of harmful reaction products due at least in part to a low output impedance of the voltage source 22 of the stimulator. At Step 74, feedback can be provided related to a change in tissue resistance due to the stimulation. For example, the feedback can be provided by a feedback circuit 26 shown in FIG. 3. The feedback can include a sampling of a power delivered to the biological tissue, and comparing a RMS voltage to a constant set point voltage. At 78, a parameter (e.g., a gain of the variable gain amplifier 24) related to the current can be changed in response to the feedback. Changing the parameter can ensure that the constant current is applied to the biological tissue, even when the tissue resistance changes. The sampling is conducted over a time window, instead of instantaneously, assuming that the tissue resistance changes more slowly than an integration time of the feedback.

From the above description, those skilled in the art will perceive improvements, changes and modifications. Such improvements, changes and modifications are within the skill of one in the art and are intended to be covered by the appended claims.

The following is claimed:
1. A method comprising:
   generating a set point voltage;
   determining a voltage delivered to a load by sampling a current into the load at different times over a time period; and
   estimating a power based on the current into the load over the time period;
   comparing the voltage delivered to the load to the set point voltage; and
   adjusting a gain of an adjustable gain amplifier based on a difference between the voltage delivered to the load and the set point voltage so that a current power output to the load remains constant.
2. The method of claim 1, wherein the current into the load is an analog current.
3. The method of claim 1, wherein the current into the load is a digital current.
4. The method of claim 1, wherein the load provides a sampled variable comprising at least one of heart rate, tissue perfusion, and ion level.
5. The method of claim 4, wherein the current power output comprises a current for neural stimulation.
6. The method of claim 1, wherein the load provides a sampled variable comprising a detected magnetic field.
7. The method of claim 1, wherein the estimating comprises calculating a root mean square of the current into the load.
8. The method of claim 1, further comprising reducing charge accumulation at a tissue-electrode interface, wherein the load is tissue.
9. The method of claim 1, wherein the current power is independent of an impedance of the load when the impedance of the load changes more slowly than a rate at which the gain of the adjustable gain amplifier is adjusted.

* * * * *